(12) United States Patent
Garcia

(10) Patent No.: US 6,589,218 B2
(45) Date of Patent: Jul. 8, 2003

(54) SUCTION DEVICE FOR REMOVING MATERIAL FROM SKIN PORES

(76) Inventor: Teddy Garcia, 921 Blanding Blvd., Orange Park, FL (US) 32065

( * ) Notice: Subject to any disclaimer, the term of this patent is extended or adjusted under 35 U.S.C. 154(b) by 32 days.

(21) Appl. No.: 09/768,076

(22) Filed: Jan. 23, 2001

(65) Prior Publication Data

US 2002/0099343 A1 Jul. 25, 2002

(51) Int. Cl.[7] .............................................. A61M 1/00
(52) U.S. Cl. ..................................... 604/313; 604/289
(58) Field of Search ............................... 604/315, 313, 604/317, 311, 118, 119, 35, 902; 606/131; 600/562–565

(56) References Cited

U.S. PATENT DOCUMENTS

| | | | |
|---|---|---|---|
| 1,732,310 A | | 10/1929 | Naibert |
| 2,267,636 A | | 12/1941 | Benton |
| 3,794,035 A | | 2/1974 | Brenner |
| 4,378,804 A | * | 4/1983 | Cortese, Jr. ..................... 15/23 |
| 4,393,879 A | * | 7/1983 | Milgrom .................. 435/309.1 |
| 4,573,965 A | * | 3/1986 | Russo ........................ 604/128 |
| 4,900,316 A | * | 2/1990 | Yamamoto .................. 239/310 |
| 5,624,416 A | | 4/1997 | Schatz |
| 6,019,749 A | * | 2/2000 | Fields et al. ................. 604/289 |
| 6,179,807 B1 | * | 1/2001 | Henniges et al. ............. 604/35 |
| 6,319,211 B1 | * | 11/2001 | Ito et al. ..................... 132/320 |
| 2001/0041848 A1 | * | 11/2001 | Ito et al. ........................ 601/6 |

* cited by examiner

*Primary Examiner*—Weilun Lo
*Assistant Examiner*—Linh Truong
(74) *Attorney, Agent, or Firm*—Thomas C. Saitta; Matthew W. Baca

(57) ABSTRACT

A device for suctioning material from skin pores, the device having a tip member, an elongated grip body having at least a transparent section, and a filter cartridge having at least a transparent section, with a filter disposed within the filter cartridge which allows passage of air but blocks passage of material, such that material extracted from the skin pores is observable as it passes through the grip body and is visible on the surface of the filter.

13 Claims, 2 Drawing Sheets

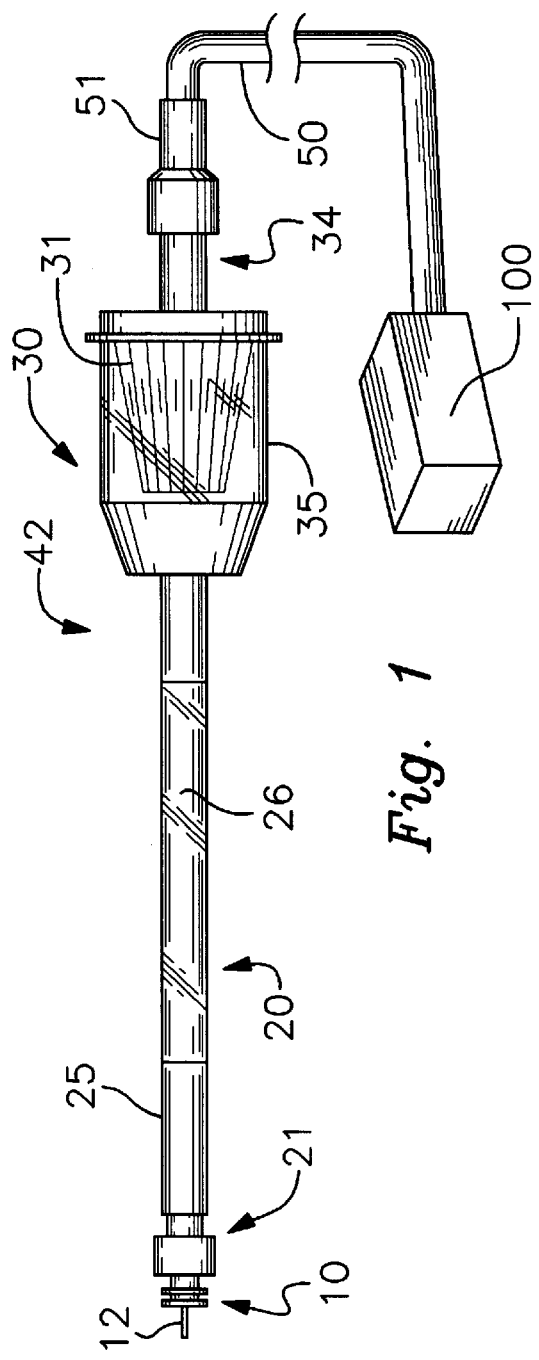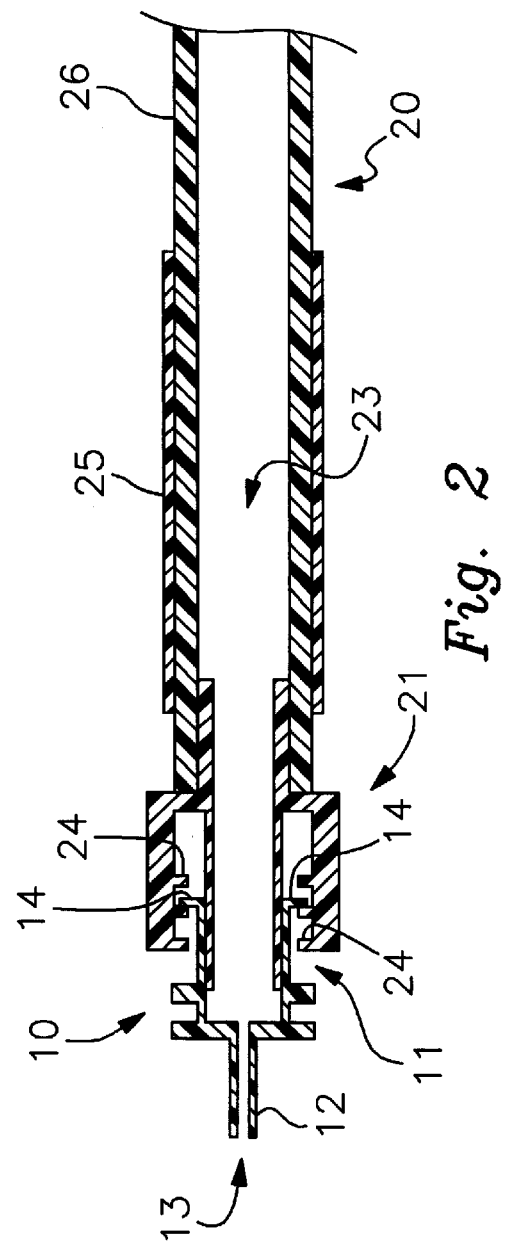

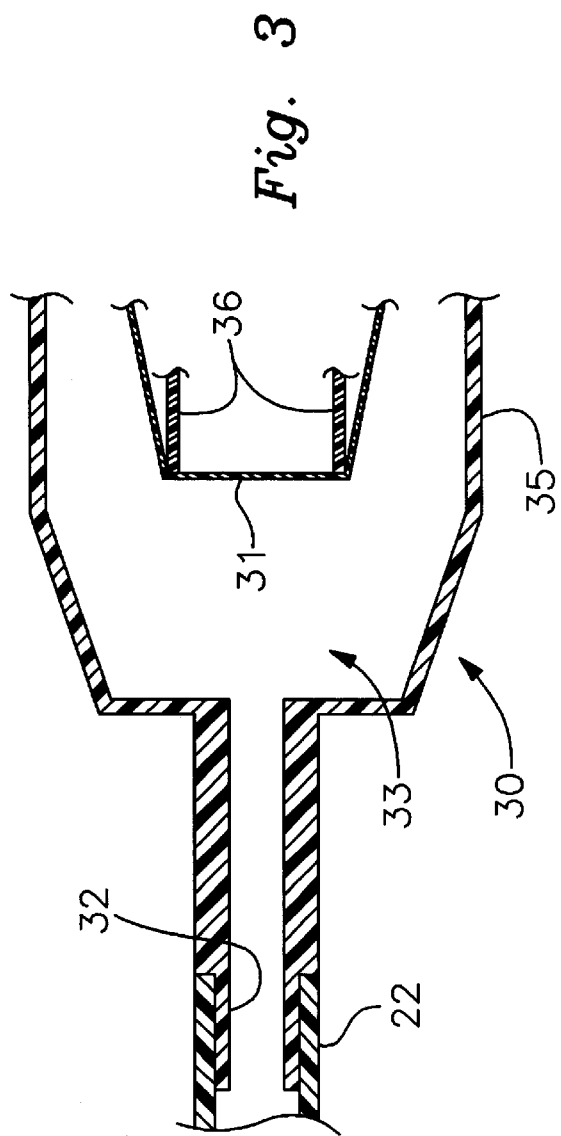
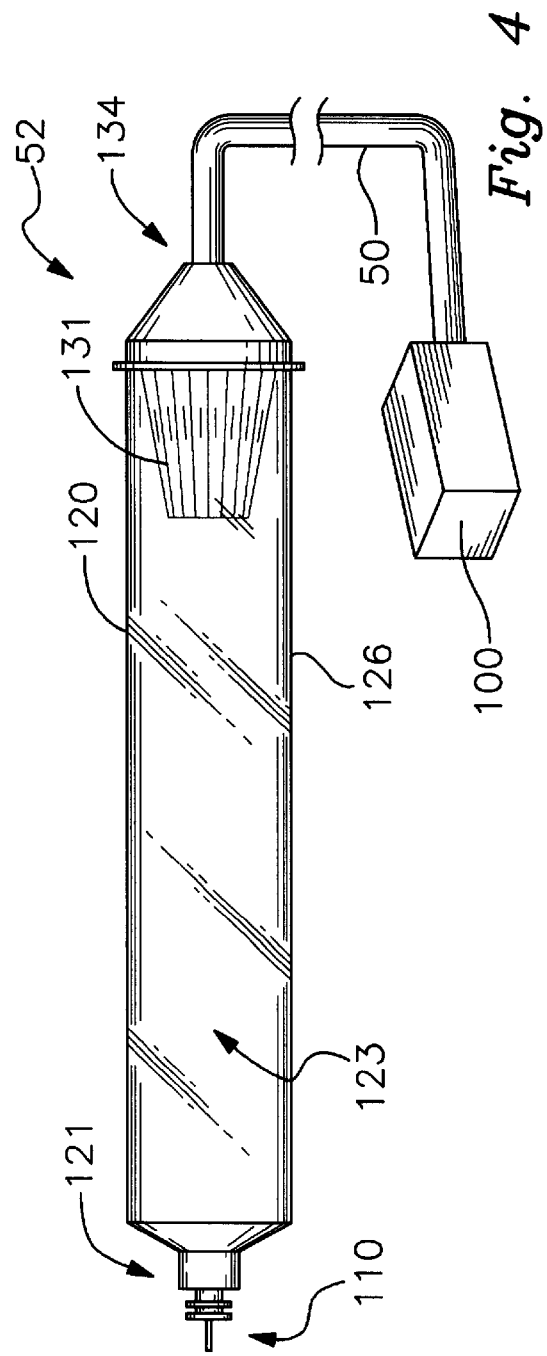

SUCTION DEVICE FOR REMOVING MATERIAL FROM SKIN PORES

BACKGROUND OF THE INVENTION

This invention relates generally to the field of devices which are used to clean or remove material from skin pores, such as sebum residues, dirt, bacteria, whiteheads, blackheads, etc., and more particularly the invention relates to such devices which utilize suction to accomplish the task.

When materials become trapped within skin pores, whether internally produced such as sebum or externally contacted such as dirt or bacteria, the natural flow of the pore is blocked and undesirable skin blemishes or conditions develop, such as pimples, white heads or blackheads, also known as comedomes, or acne. In order to relieve the problem, the skin pores must be cleared of the undesirable materials so that the natural expulsion process of the pore is restored and so that medication can be received by the pore.

A well known methodology for addressing this problem is through the use of suction devices which have relatively small suction tips. The tip is pressed against the pore and a vacuum is produced within the device, the internal vacuum extracting the material from within the pore and into the device. An early example of this type of device is shown in U.S. Pat. No. 2,267,636 to Benton, wherein a spring-biased plunger arrangement is provided. The tip of the apparatus is applied to the pore to be cleaned and the internal plunger is retracted to create suction through the tip, drawing the material into the device. The material is later expelled from the device by moving the plunger forward. Because mechanical manipulation of the device is required for its operation and because the suction effect is non-continuous, the efficiency of the device is relatively limited, since improper placement or movement of the tip during the retraction operation may fail to remove the material from the pore, necessitating multiple attempts to cleanse a single pore. To solve this problem, devices have been developed which utilize a continuous suction, produced mechanically by vacuum pumps or through liquid flow suction systems. For example, Naibert in U.S. Pat. No. 1,732,310 and Brenner in U.S. Pat. No. 3,794,035 show skin suction devices which utilize mechanical means to create a continuous suction through a nozzle pressed against the skin. Schatz in U.S. Pat. No. 5,624,416 shows a suction device which includes a pinching jaw at the distal tip, where the partial vacuum is created by connecting a conduit to a water flow in a manner whereby the water flow creates a partial vacuum in the conduit. Fields er al. in U.S. Pat. No. 6,019,749 shows a suction device where a first suction means is used to draw the skin around the pore outward and a section suction means, internal to the first, is used to draw the material from the pore.

It is an object of this invention to provide a pore cleaning device which utilizes suction to extract material from within the skin pore, the device being an improvement over the known devices used to accomplish this task. To this end, it is a further object to provide such a device which is hand-held and which is operationally simple. It is a further object to provide such a device where the main housing is an elongated tube for easy grasping by the operator, where the tips are removable from the housing, and where a filter is provided to collect the material removed from the pores. It is a further object to provide such a device which provides a visual indication to the operator that the device is properly functioning, as well as a visual indicator of the amount of material removed from successive pores, which is accomplished by composing the elongated tube portion and the filter housing from transparent material.

SUMMARY OF THE INVENTION

The invention is in general a device for removing material, such as for example sebum deposits, dirt, bacteria, blackheads, whiteheads, etc., from skin pores by suctioning the material from the pores. The invention comprises in general a hand-held body of elongated shape, the body being tubular and adapted to receive and retain a tip member on its distal end. The tip member has a distal nozzle and a bore of relatively small diameter, the tip bore communicating with the bore of the body. A filter means is disposed either within the body or within a filter cartridge housing connected in communicating manner with the body. Suction means are provided to create a partial vacuum within the device, such that material is drawn from the skin pores through the tip member and the body, where it is entrapped by the filter. At least a portion of the body, and at least a portion of the separate filter cartridge if present, on the upstream side of the filter is formed of a transparent material so that the filter is exposed and so that the operator can monitor the efficacy of the device during use, as well as providing visual evidence of the amount and type of material removed by the device. The tip member may be removable, such that disposable tip members can be used.

BRIEF DESCRIPTION OF THE DRAWINGS

FIG. 1 is a plan view of a first embodiment of the invention, where the filter is retained within a filter cartridge housing connected to the elongated gripping body.

FIG. 2 is a cross-sectional view taken along line II—II of FIG. 1, showing the distal portion of the invention.

FIG. 3 is a cross-sectional view taken along line III—III of FIG. 1, showing the distal portion of the filter cartridge housing.

FIG. 4 is a plan view of a second embodiment of the invention, where the filter is provided as integral with the elongated body.

DETAILED DESCRIPTION OF THE INVENTION

With reference to the drawings, the invention will now be described in detail with regard for the best mode and the preferred embodiments. In its most general aspect, the invention is a hand-held device for suctioning material from skin pores. In a more particularized aspect, the invention is such a device comprising a tip member 10, an elongated grip body 20, a filter cartridge or housing 30 containing filter means 31, suction means 100 for creating a partial vacuum within the device, and conduit means 50 connecting the device to the suction means 100, whereby material may be extracted from a skin pore by pressing the tip member 10 against the skin pore with the vacuum means operating such that the material is sucked into the tip member 10 and through the grip body 20 to be retained by the filter means 31. In an alternative embodiment, the filter means 31 is provided as an integral component of the grip body 20.

In the following discussion, the term distal shall be taken to refer to the end of the device which is applied to the skin pore or the direction toward that end, and the term proximal shall be taken to refer to the opposite end of the device, the end connected to the conduit 50 leading to the suction means 100, or that direction.

A first embodiment of the invention, as shown in FIG. 1, shows the device to be comprised of a relatively elongated applicator instrument 42 that can be readily gripped and maneuvered in an operator's hand, the applicator instrument 42 being configured to be pen-like with the majority of the device being of generally small diameter in cross-section. As depicted in FIG. 1, the applicator instrument 42 is a substantially rigid device comprising a grip body or housing member 20, a tip member 10 connected to the distal end of the grip body 20 in a communicating manner, and a filter cartridge 30 connected to the proximal end of the grip body 20. As further depicted in FIG. 1, the tip member 10, the grip body 20, and the filter cartridge 30 are mutually coupled such that a longitudinal tip bore 13 and a grip body bore 23 are axially aligned to form an externally visible straight inline suction bore through the applicator instrument 42 extending from a tip nozzle 12 on the end of tip member 10 to the filter means 31. Conduit means 50 are joined to the applicator instrument 42 at the proximal end of the filter cartridge 30 to provide communication with a vacuum or suction producing means 100. Suction means 100 may be any suitable device, system or apparatus known in the art for producing a partial vacuum within the device, such that air and material is drawn through the tip member 10 and grip body 20, such that air is pulled through filter means 31 while solid or liquid material is deposited onto the distal surface of the filter means 31. Suction means 100 may comprise a powered vacuum device containing an electric or fuel powered motor, or preferably comprises a suction apparatus which operates by communication to source of water flow, where the water flow creates the partial vacuum. Most preferably, suction means 100 is capable of producing continuous suction through the device, and it is also contemplated that actuating switches, such as a foot pedal or the like, could be employed interrupt the continuous suction or to provide a pulsing suction.

The tip member 10 comprises a relatively rigid, distal tip nozzle 12 of relatively small diameter, preferably about 1/16 inches in outer diameter, and tip joining means 11 for connecting the tip member 10 to the grip body 20, most preferably in a temporary or removable manner, with a longitudinal bore 13 passing completely through the tip member 10. Connecting the tip member 10 to the grip body 20 in a temporary manner allows multiple tip members 10 to be used with the same grip body 20, whether for purposes of changing the size of the tip nozzle 12 or bore 13 as required for different applications, or to allow for the use of disposable tip members 10 such that the grip body 20 may be reused. Tip joining means 11 may comprise elements of any known mechanical interlocking method, and as shown comprise a pair of flanges 14 which cooperate with tip receiving means 21 comprising a pair of helical threads 24 disposed within the tip receiving means 21 on the distal end of the grip body 20, as best seen in FIG. 2—a construction commonly known as a Luer lock. To connect a tip member 10, the flanges 14 are inserted into the tip receiving means 21 and the tip member 10 is rotated until it is properly secured. Removal for replacement simply entails unscrewing the tip member 10. The bore 13 of the tip member 10 is enlarged in diameter in the proximal section of the tip member 10. The provision of a relatively small in cross-section bore 13 in the tip nozzle 12 increases the drawing power of the suction through the device.

The tip receiving means 21 is joined to or is formed integral with the grip body 20 at the distal end. The grip body 20 is an elongated tubular member, having for example a length of approximately 4.25 inches and a cross-sectional diameter of approximately 3/8 inches, with a longitudinal bore 23 extending the entire length of the grip body 20. Filter cartridge receiving means 22 for receiving the filter cartridge 30 in either a permanent or temporary manner is provided at the proximal end of the grip body 20, and in a most simple form as shown in FIG. 3 comprises the open end of the grip body 20. Enhanced gripping means 25, such as a sleeve made of polymer or polymer foam material, may be externally mounted onto the grip body 20 towards its distal end to assist in securing the device in the operator's hand.

The grip body 20 is provided with a transparent section 26, which preferably comprises the majority or the entirety of the grip body 20, and is most easily formed by constructing the grip body 20 from a transparent plastic material.

A filter cartridge or housing 30 is joined in communicating manner by body joining means 32 to the proximal end of the grip body 20, preferably in a temporary manner such that the filter cartridge 30 may be removed and replaced. As shown in FIG. 3, the body joining means 32 may simply comprise a reduced diameter segment or tube inserted into the proximal end of the grip body 20 for a friction fit. Alternatively, other mechanical interlocking structures may be utilized. The cross-sectional diameter of the filter cartridge 30 is of much greater dimension than the cross-sectional diameter of the grip body 20, as shown in FIGS. 1 and 3, such that relatively large filter means 31 may be retained within the cartridge 30. For example, with a grip body 20 diameter of about 3/8 inches, a filter cartridge 30 diameter of about 1 and 1/8 inches may be utilized. Alternatively, the diameter of the filter cartridge 30 could be reduced to be equal or even smaller than that of the grip body 20. Filter means 31 may be any suitable filtering media which allows for the passage of air therethrough, such that a suction may be created within the device, while simultaneously blocking passage of solid materials and some or all liquids, and as shown comprises a pleated, conical filter composed of a paper material supported by an internal frame member 36 disposed within the filter chamber 33. The filter cartridge 30 is provided with conduit joining means 34, which may simply comprise a tube of relatively small diameter, for connecting the filter cartridge 30 to a connector fitting 51 or directly to a flexible conduit means 50, preferably medical grade polymer tubing, which in turn is connected in communicating manner to the suction means 100.

The filter cartridge 30 is provided with a transparent section 35, which preferably comprises the majority or the entirety of the filter cartridge 30, in order to visually expose the upstream or distal side of the filter means 31, and is most easily formed by constructing the filter cartridge 30 from a transparent plastic material.

An alternative embodiment for the invention is shown in FIG. 4, where an applicator instrument 52 includes the filter means 131 disposed within the grip body 120 itself, such that a separate housing for the filter means 131 is not necessary, the grip body 120 having a relatively large diameter interior chamber 123. A tip member 110 is joined to the distal end of the grip body 120 by tip receiving means 121, in any manner as previously discussed relative to the embodiment of FIG. 1. Conduit joining means 134 is provided for connecting the proximal end of the grip body 120 to the conduit means 50 and suction means 100. The grip body 120 is provided with a transparent section 126 which at a minimum exposes the filter means 131 to external view, and which preferably extends over a significant portion or the entirety of the grip body 120. In this embodiment, the cross-sectional diameter of the grip body 120 may be about 1 and 1/8 inches, or may be made larger or smaller if desired. A large diameter allows for greater filter means 131 surface area, while a smaller diameter provides a device which is easier to grip.

To use the device, the suction means 100 is activated such that a partial vacuum is created within the device, air being drawn into the tip nozzle 12 and bore 13, through the bore 23 of the grip body 20, into the chamber 33 of the filter cartridge 30, through the filter means 31, and through conduit means 50. The distal end of the tip nozzle 12 is applied to the skin pore, and material within the pore is extracted. The solid or liquid material passes through transparent section 25 of the grip body 20 and thereby provides a visible indication to the operator that the nozzle 12 is properly positioned and that material is being removed from the pore. When material is no longer observed passing through the grip body 20, the pore is fully cleaned. In addition, the extracted material and liquids are deposited onto the distal side of the filter means 31, where it is visible through the transparent section 35 of the filter cartridge 30, such that the operator can ascertain the amount and nature of the material being removed, as well as providing a collector to demonstrate to the patient the efficiency of the treatment. Where the tip member 10 is temporarily joined to the grip body 20, the operator may replace the tip member 10 as desired. Likewise, where the filter cartridge 30 is temporarily connected to the grip body 20, the filter cartridge 30 in its entirety or the filter means 31 alone my be replaced as desired. For an integral unit with replaceable tip members 110 such as shown in FIG. 3, the entire device is considered to be disposable, although it would also be possible to construct the grip body 120 to have a removable proximal end to enable replacement of the filter means 31.

I claim:

1. A device for suctioning materials from skin pores, said device comprising:

a tip member comprising a tip nozzle and a tip bore;

a grip body comprising a grip body bore and connected in communicating manner to said tip member, said grip body further comprising a transparent section, such that material passing through said grip body bore is exposed for visual observation;

a filter cartridge containing a filter means for blocking passage of solid material therethrough while allowing passage of air, said filter cartridge comprising a chamber and a transparent section, such that said filter means is exposed for visual observation, said filter cartridge connected in communicating manner to said grip body bore;

wherein said tip member, said grip body, and said filter cartridge are mutually coupled to form a single, substantially rigid applicator instrument wherein said tip bore and said grip body bore are axially aligned to form a straight inline suction bore between the tip nozzle and said filter means, said straight inline suction bore externally visible through the transparent sections of said grip body and said filter cartridge; and whereby said device can be connected in communicating manner to a means for producing suction such that a partial vacuum is drawn through said device, such that air is drawn through said straight inline suction bore and said filter means within said filter cartridge chamber, and such that material from a skin pore is drawn through said straight inline suction bore and deposited onto said filter means.

2. The device of claim 1, wherein said tip member is removable from said grip body.

3. The device of claim 1, wherein said grip body is an elongated tube.

4. The device of claim 1, where the cross-sectional diameter of said grip body is less than the cross-sectional diameter of said filter cartridge.

5. The device of claim 1, where said filter cartridge is removable from said grip body.

6. The device of claim 1, where said transparent section of said filter cartridge comprises the entire said filter cartridge.

7. The device of claim 1, where said transparent section of said grip body comprises the entire said grip body.

8. The device of claim 7, where said transparent section of said filter cartridge comprises the entire said filter cartridge.

9. The device of claim 1, further comprising conduit means to connect said filter cartridge to said suction means.

10. A device for suctioning materials from skin pores, said device comprising:

a tip member comprising a tip nozzle and a tip bore;

a grip body connected in communicating manner to said tip member and comprising a grip body bore, a filter means for blocking passage of solid material therethrough while allowing passage of air, and a transparent section comprising the entire said grip body, such that said filter means is exposed for visual observation, wherein said tip member and said grip body form a single, substantially rigid applicator instrument having a straight inline suction bore comprising said tip bore and said grip body bore and extending between the tip nozzle and said filter means, said straight inline suction bore externally visible through the transparent section of said grip body;

whereby said device can be connected in communicating manner to a means for producing suction such that a partial vacuum is drawn through said device, such that air is drawn through said tip bore, said grip body bore and said filter means, and such that material from a skin pore is drawn through said tip bore, said grip body bore and deposited onto said filter means.

11. The device of claim 10, wherein said tip member is removable from said grip body.

12. The device of claim 10, wherein said grip body is an elongated tube.

13. A device for suctioning materials from skin pores, said device comprising:

a tip member comprising a tip nozzle and tip joining means;

an elongated, transparent grip body including a transparent section and further comprising tip receiving means and filter cartridge receiving means, and connected in communicating manner to said tip member;

a filter cartridge containing a filter means for blocking passage of solid material therethrough while allowing passage of air, said filter cartridge comprising grip body joining means, conduit joining means, a chamber and a transparent section, such that said filter means is exposed for visual observation, said filter cartridge connected in communicating manner to said grip body, wherein said tip member, said grip body, and said filter cartridge are mutually coupled to form a single, substantially rigid applicator instrument having a straight inline suction bore comprising said tip bore and said grip body bore and extending between the tip nozzle and said filter means, said straight inline suction bore externally visible through the transparent sections of said grip body and said filter cartridge;

means for producing suction such that a partial vacuum is drawn through said device; and conduit means for connecting said suction means to said filter cartridge means in communicating manner;

whereby air is drawn through said straight inline suction bore and said filter means within said filter cartridge chamber, and whereby material from a skin pore is drawn through said straight inline suction bore and deposited onto said filter means.

* * * * *